(12) United States Patent
Easton et al.

(10) Patent No.: US 10,168,256 B2
(45) Date of Patent: Jan. 1, 2019

(54) SAMPLE PROBE INLET FLOW SYSTEM

(71) Applicants: SMITHS DETECTION-WATFORD LIMITED, Bushey, Watford, Hertfordshire (GB); Matt Easton, Bushey, Watford, Hertfordshire (GB); Stephen Taylor, Bushey, Watford, Hertfordshire (GB)

(72) Inventors: Matt Easton, Watford (GB); Stephen Taylor, Watford (GB)

(73) Assignee: SMITHS DETECTION-WATFORD LIMITED, Hertfordshire (GB)

( * ) Notice: Subject to any disclaimer, the term of this patent is extended or adjusted under 35 U.S.C. 154(b) by 669 days.

(21) Appl. No.: 14/430,184

(22) PCT Filed: Sep. 20, 2013

(86) PCT No.: PCT/GB2013/052474
§ 371 (c)(1),
(2) Date: Apr. 30, 2015

(87) PCT Pub. No.: WO2014/045056
PCT Pub. Date: Mar. 27, 2014

(65) Prior Publication Data
US 2015/0300927 A1 Oct. 22, 2015

Related U.S. Application Data

(60) Provisional application No. 61/704,036, filed on Sep. 21, 2012.

(51) Int. Cl.
*G01N 1/22* (2006.01)
*G01N 27/62* (2006.01)
*G01N 1/24* (2006.01)

(52) U.S. Cl.
CPC ............. *G01N 1/2273* (2013.01); *G01N 1/24* (2013.01); *G01N 27/622* (2013.01); *G01N 2001/2285* (2013.01); *G01N 2001/245* (2013.01)

(58) Field of Classification Search
None
See application file for complete search history.

(56) References Cited

U.S. PATENT DOCUMENTS

| | | | | |
|---|---|---|---|---|
| 4,596,156 A | * | 6/1986 | Shimizu | G01N 1/2252 137/599.03 |
| 4,624,150 A | * | 11/1986 | Shimizu | G01N 35/1095 73/864.81 |
| 5,907,109 A | * | 5/1999 | Tedeschi | G01N 1/26 73/864.73 |
| 7,690,276 B1 | | 4/2010 | Wise | |

(Continued)

FOREIGN PATENT DOCUMENTS

| | | | |
|---|---|---|---|
| RU | 2107289 | * | 3/1998 |
| RU | 2107289 C1 | | 3/1998 |

(Continued)

OTHER PUBLICATIONS

Mexican Office Action dated Oct. 26, 2016 for Mexican Appln. No. MX/a/2015/003527.
(Continued)

*Primary Examiner* — Robert R Raevis
(74) *Attorney, Agent, or Firm* — Kevin E. West; Advent, LLP

(57) ABSTRACT

An apparatus includes a sample receiving port and an inlet assembly configured to be positioned adjacent to the sample receiving port. The inlet assembly defines a volume for receiving a sample and includes a gap that defines an extraction port. The extraction port is configured to extract one fluid flow to facilitate another fluid flow toward the
(Continued)

sample receiving port. The extraction port can be configured as an annular flow port around the sample receiving port. In some instances, the apparatus also includes a curtain port positioned apart from the sample receiving port and the extraction port. The curtain port can be used to guide fluid away from interior surfaces of the inlet assembly and toward the sample receiving port, and/or to provide an environment of controlled air, and/or to isolate the sample receiving port from external sources of contamination.

10 Claims, 6 Drawing Sheets

(56) References Cited

U.S. PATENT DOCUMENTS

2002/0134174 A1* 9/2002 Silvis .................. G01N 1/2252
  73/863.81
2011/0132108 A1    6/2011 Novosselov et al.

FOREIGN PATENT DOCUMENTS

| RU | 2126149 C1    | 10/1999 |
| WO | 199014587     | 11/1990 |
| WO | 2008074981    | 6/2008  |
| WO | 2009001029    | 12/2008 |
| WO | 2012031082 A2 | 3/2012  |

OTHER PUBLICATIONS

International Search Report for PCT/GB2013/052474 dated Jan. 8, 2014.
Office Action and Search Report dated Sep. 14, 2017 for Russian Appln. No. 2015109719/05(015400).
Office Action dated Jun. 13, 2017 for Japanese Appln. No. 2015-532505.

* cited by examiner

SAMPLE PROBE INLET FLOW SYSTEM

BACKGROUND

Ion mobility spectrometry refers to an analytical technique that can be used to separate and identify ionized material, such as molecules and atoms. Ionized material can be identified in the gas phase based on mobility in a carrier buffer gas. Thus, an ion mobility spectrometer (IMS) can identify material from a sample of interest by ionizing the material and measuring the time it takes the resulting ions to reach a detector. An ion's time of flight is associated with its ion mobility, which relates to the mass and geometry of the material that was ionized. The output of an IMS detector can be visually represented as a spectrum of peak height versus drift time. In some instances, IMS detection is performed at an elevated temperature (e.g., above one hundred degrees Celsius (100° C.)). In other instances, IMS detection can be performed without heating. IMS detection can be used for military and security applications, e.g., to detect drugs, explosives, and so forth. IMS detection can also be used in laboratory analytical applications, and with complementary detection techniques such as mass spectrometry, liquid chromatography, and so forth.

SUMMARY

Systems and techniques for inducing fluid flow toward a sample receiving port using an extraction port are described. For example, an apparatus includes a sample receiving port and an inlet assembly configured to be positioned adjacent to the sample receiving port. The inlet assembly defines a volume for receiving a sample and includes a gap that defines an extraction port configured to be positioned adjacent to the sample receiving port. The extraction port is configured to extract one fluid flow to facilitate another fluid flow toward the sample receiving port. The extraction port can be configured as an annular flow port around the sample receiving port. In some instances, the apparatus also includes a curtain port positioned apart from the sample receiving port and the extraction port. The curtain port can be used to guide fluid away from interior surfaces of the inlet assembly and toward the sample receiving port, and/or to provide an environment of controlled air, and/or to isolate the sample receiving port from external sources of contamination.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE DRAWINGS

The detailed description is described with reference to the accompanying figures. In the figures, the left-most digit(s) of a reference number identify the figure in which the reference number first appears. The use of the same reference number in different instances in the description and the figures may indicate similar or identical items.

FIG. 1D is a partial cross-sectional side elevation view illustrating an inlet assembly including an extraction port positioned adjacent to a sampling pinhole, where the inlet assembly is used in a vapor sampling configuration in accordance with example implementations of the present disclosure.

DETAILED DESCRIPTION

Sample probes are often used with analytical instruments, such as spectrometer systems, to obtain a sample of interest and then introduce the sample to an analytical device. For example, sample probes are typically used with IMS detector systems to collect samples from a surface. A sample can then be introduced to an IMS detector using, for instance, a desorber to vaporize a portion of the sample. By heating a sample probe in front of a sampling pinhole of an IMS detector, the sample can be desorbed so that trace elements of any substances of interest can be detected by the IMS instrumentation. However, heat from a sample probe in this configuration can produce unwanted convection currents, which can transport sample material from the sample probe away from the pinhole.

In some cases, convection currents may be dependent upon gravity. Thus, the effectiveness and/or sensitivity of an IMS detector may be dependent upon the orientation of the IMS detector and/or the orientation of a sample probe when a sample is desorbed. Because operators may use IMS detectors in a variety of orientations, and, further, because sample probes may collect samples of interest unevenly (e.g., based upon angle, direction of use, and so forth), various combinations of IMS detector orientation and sample distribution on a sample probe can produce various convection currents, some of which can guide a sample away from a pinhole.

Techniques are described for directing sample material toward a sample inlet port of a detection device. For example, an inlet assembly for a sample detector can include an extraction port, and possibly a curtain port, for directing sample material toward a sampling pinhole. The sample material, which is carried along with a flow of fluid, such as air, or the like, can be directed toward the pinhole and carry sample material from, for instance, a substantial portion of the tip of a sample probe adjacent to the sampling pinhole. Further, airflow through the extraction port can carry material away from the interior walls of the inlet assembly and exhaust the air from the detection device using the extraction port. This may be particularly useful when the interior walls of the inlet assembly become coated with vapor, which can include material from previous samples, which could otherwise contaminate successive samples. Techniques in accordance with the present disclosure can reduce the dependence of sample concentration on device orientation and/or sample distribution. This can reduce the difference between minimum and maximum concentration and aid the achievement of reasonable limits of detection under various conditions. Further, when a curtain port is included, a controlled sampling environment can be provided, isolating a sample inlet from possible contaminants outside a detector.

Figure 1A:
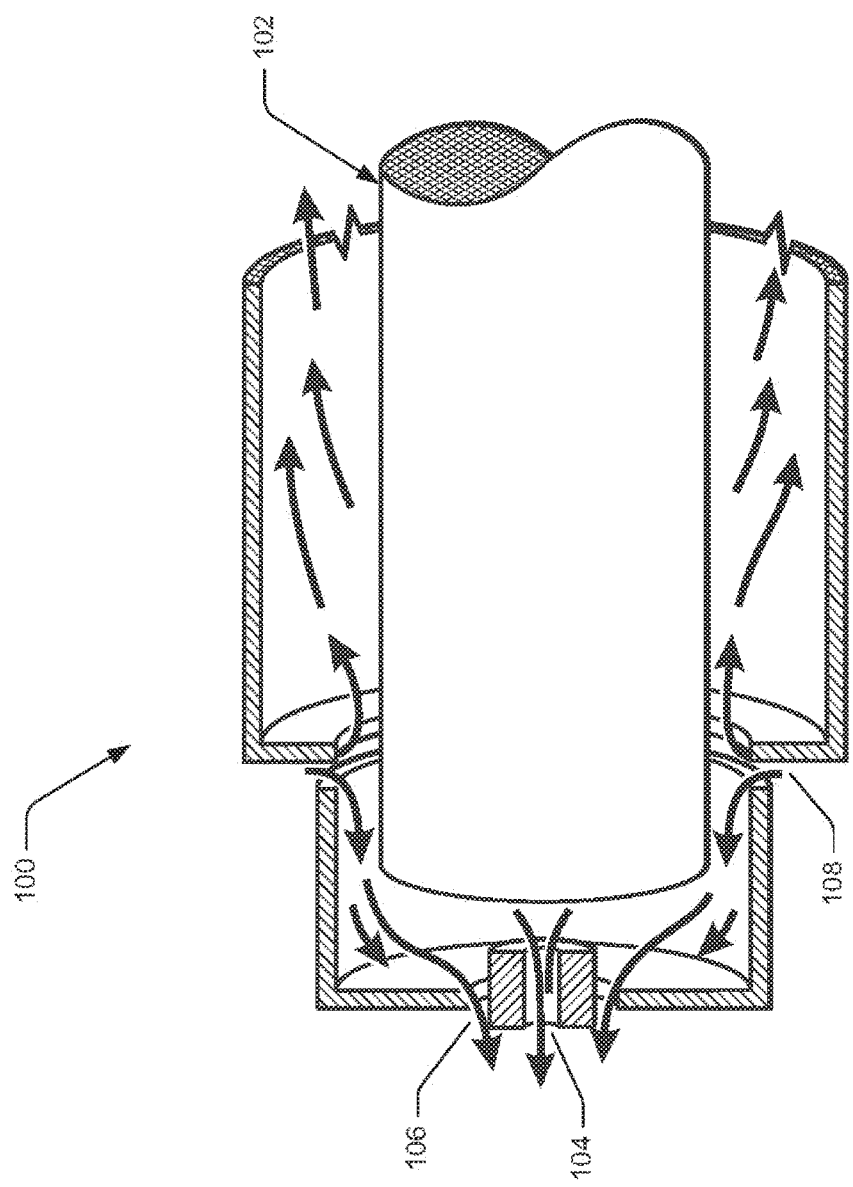
FIG. 1A is a partial cross-sectional side elevation view illustrating an inlet assembly including an extraction port positioned adjacent to a sampling pinhole, and a curtain port separated from the extraction port, where a sample probe is positioned within the inlet assembly in accordance with example implementations of the present disclosure.
Figure 1B:
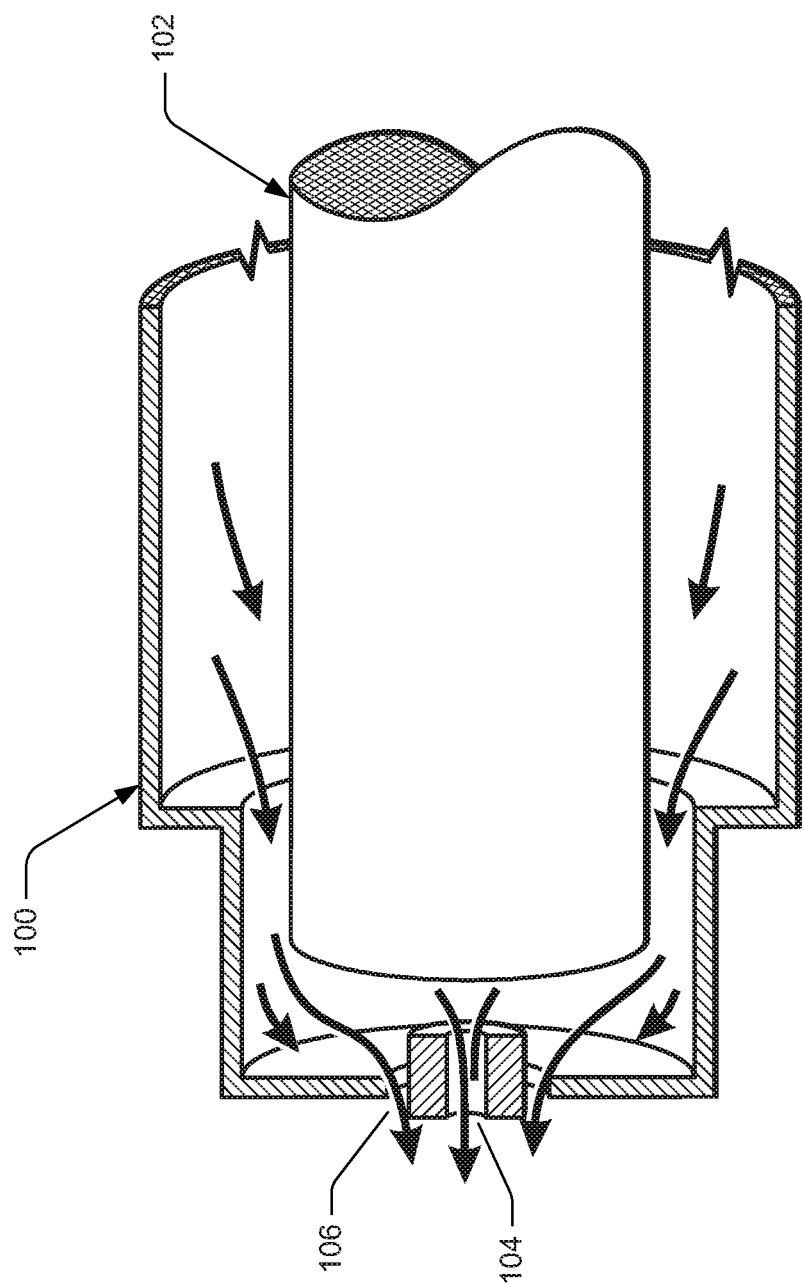
FIG. 1B is a partial cross-sectional side elevation view illustrating an inlet assembly including an extraction port positioned adjacent to a sampling pinhole, where a sample probe is positioned within the inlet assembly in accordance with example implementations of the present disclosure.
Figure 1C:
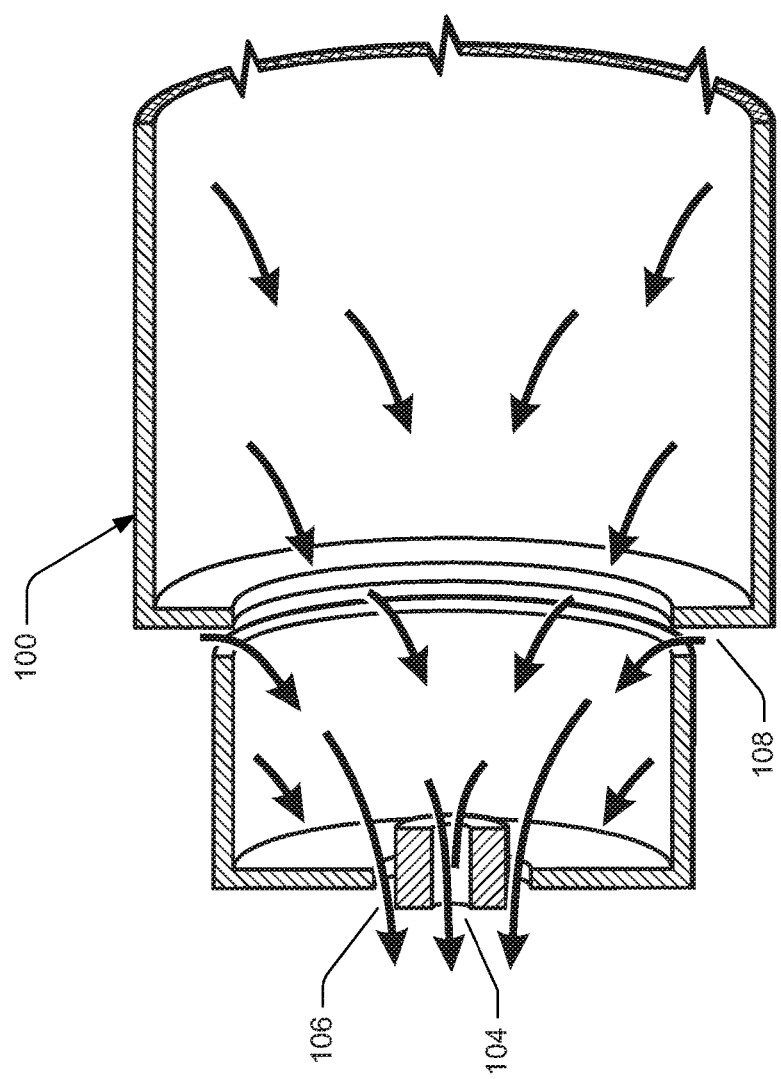
FIG. 1C is a partial cross-sectional side elevation view illustrating an inlet assembly including an extraction port positioned adjacent to a sampling pinhole, and a curtain port separated from the extraction port, where the inlet assembly is used in a vapor sampling configuration in accordance with example implementations of the present disclosure.
Figure 10:
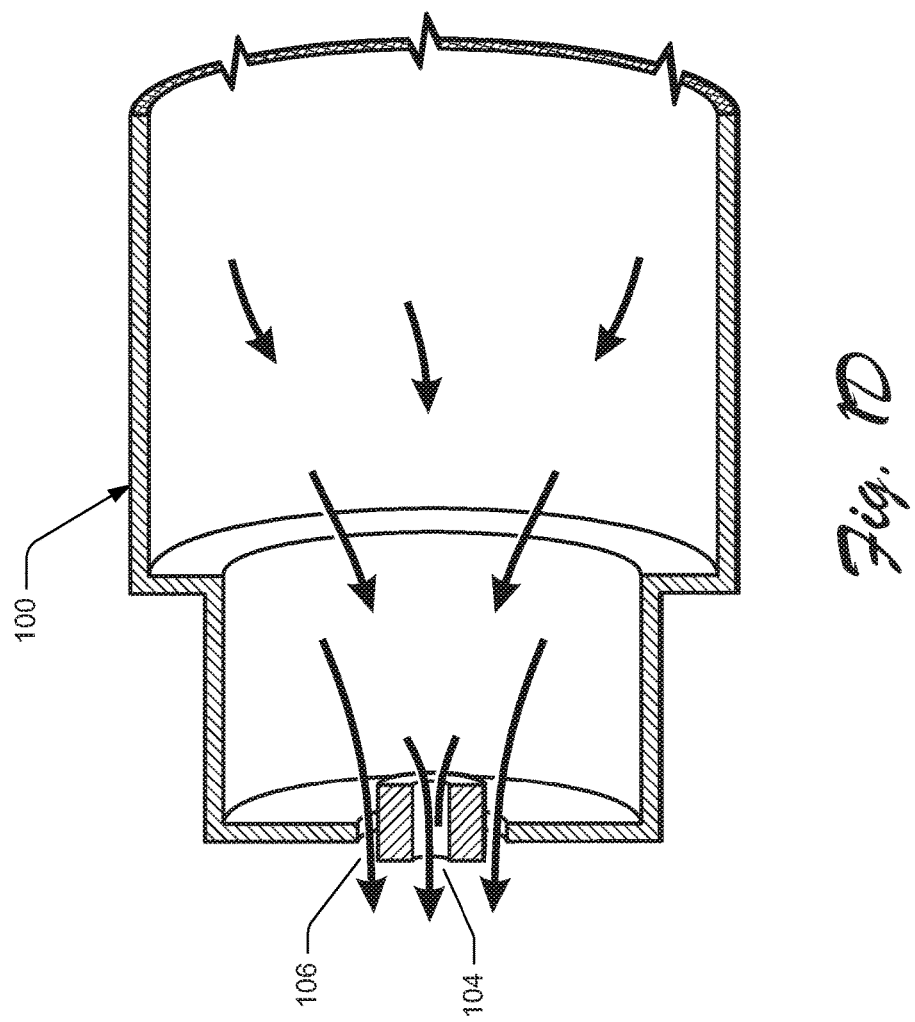
Figure 2A:
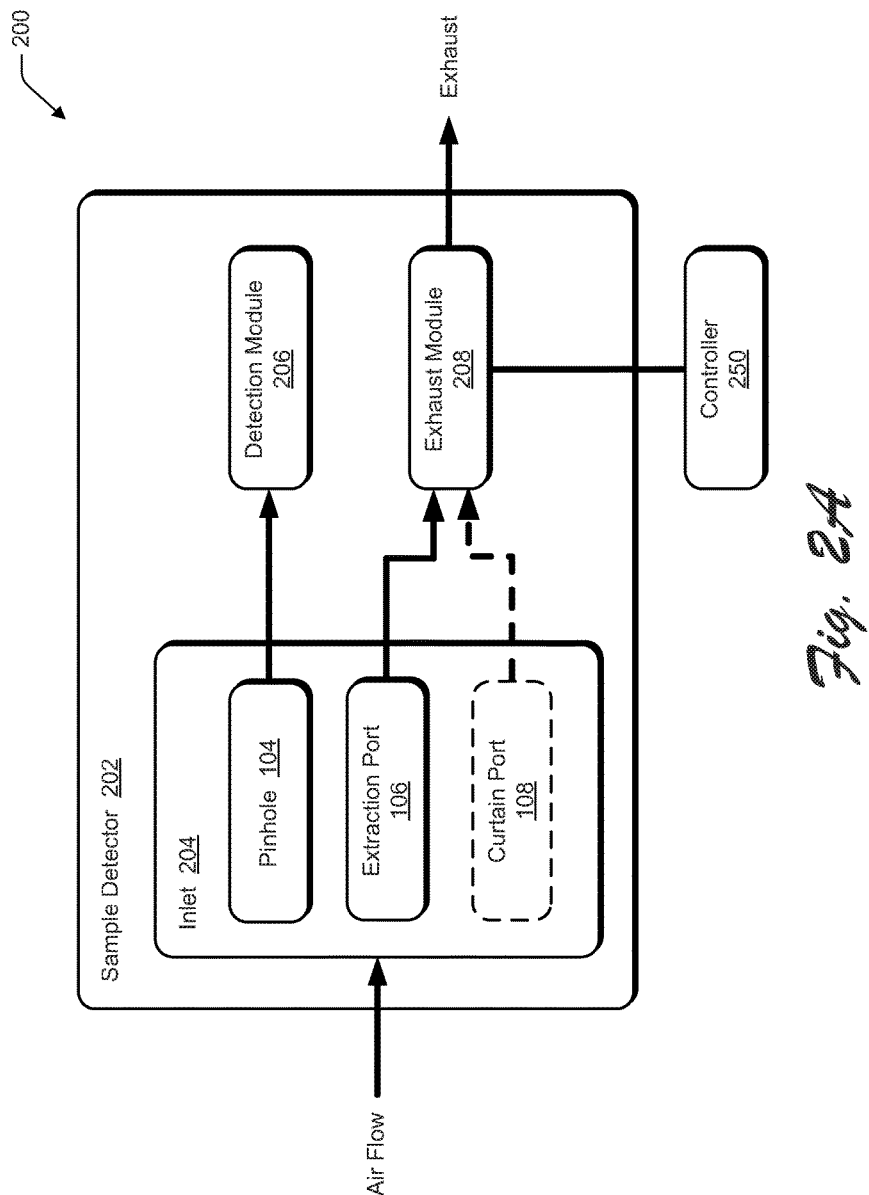
FIG. 2A is a diagrammatic illustration of a system including a controller operatively coupled with an exhaust module of a sample detector, where the controller can be used to control the operation of the exhaust module to facilitate operation of an inlet of the sample detector in one or more of a sample probe configuration and a vapor sampling configuration in accordance with example implementations of the present disclosure.

FIGS. 1A through 1D illustrate inlet assemblies 100, which can be used with, for example, a sample detector, such as the IMS systems 200 illustrated in FIG. 2. For example, an inlet assembly 100 can be used with an FMS system 200 to provide the IMS system 200 with samples of interest (e.g., from a sample probe 102 as illustrated in FIGS. 1A and 1B, and/or from the surrounding environment as illustrated in FIGS. 1C and 1D). In implementations, a sample can be received by the IMS systems 200 through a sample receiving port (e.g., a sampling pinhole 104. The inlet assemblies 100 include an extraction port 106, which may be situated adjacent to the pinhole 104. When a sample probe 102 is inserted in an inlet assembly 100, the pinhole 104 and the extraction port 106 are positioned near the sample probe 102.

The extraction port 106 is used to draw fluid flow (e.g., airflow) toward the pinhole 104. For example, as fluid is drawn through the extraction port 106 in the direction of, for example, a sample detector, fluid will also be drawn toward the pinhole 104. In some instances, the extraction port 106 is configured as an annular flow port defined by the inlet assembly 100 adjacent to and coplanar with the pinhole 104. For instance, the extraction port 106 can be circumferentially disposed about the pinhole 104. The flow of fluid is thus arranged to be substantially uniform around the annulus of the extraction port 106 so that fluid flow toward the pinhole 104 is at least substantially independent of the directional orientation of the inlet assembly 100 and/or the sample probe 102. The uniform flow can be produced by, for example, narrow air spaces with circular flow restrictions surrounding each port. In implementations where two or more pinholes 104 are included, two or more extraction ports 106 can be included, one for each pinhole.

In implementations, the flow rate of fluid through the extraction port 106 can be selected to be sufficiently high to overcome convection currents generated by, for example, a desorber. In this manner, the fluid flow toward the pinhole 104 can be at least substantially independent of the directional orientation of the inlet assembly 100 and/or the sample probe 102. In other instances, the extraction port 106 can be used when a sample detector is operated in a vapor sampling (sniffing) configuration. In this configuration, a sample probe 102 is not necessarily used to provide a sample of interest. Rather, air from outside the detector (e.g., ambient air) can be drawn in through the inlet assembly 100. This airflow can be generated and/or facilitated by fluid flow through the extraction port 106.

While the present disclosure and the accompanying figures describe an annular extraction port 106 configured to provide substantially uniform airflow around the periphery of the pinhole 104, it should be noted that this particular configuration is provided by way of example only and is not meant to be restrictive of the present disclosure. Thus, in other implementations, other variously-shaped extraction ports may be provided, including square-shaped apertures, rectangular-shaped apertures, elliptical-shaped apertures, diamond-shaped apertures, and so forth. Further, more than one aperture may be provided, including two apertures, three apertures, four apertures, and so forth. These additional apertures may be variously-shaped (e.g., as previously described). Further, it should be noted that the flow generated by these other aperture configurations may not be substantially uniform.

In some instances, two or more separate flow ports can be provided. For example, a curtain port 108 can be included with the inlet assembly 100. The curtain port 108 can be positioned so that it substantially surrounds a tip of the sample probe 102 when the sample probe 102 is positioned in the inlet assembly 100. The curtain port 108 is used to draw fluid flow (e.g., airflow) into the interior of the inlet assembly 100. In some instances, the curtain port 108 is configured as an annular flow port defined by the inlet assembly 100 adjacent to the tip of the sample probe 102 when the sample probe 102 is inserted in the inlet assembly 100. For instance, the curtain port 108 can be circumferentially disposed about a tip of the sample probe 102. The flow of fluid is thus arranged to be substantially uniform around the annulus of the curtain port 108 so that fluid flow toward the pinhole 104 is at least substantially independent of the directional orientation of the inlet assembly 100 and/or the sample probe 102. In implementations where two or more pinholes 104 are included, two or more extraction ports 106 and two or more curtain ports 108 can be included, one extraction port 106 and one curtain port 108 for each pinhole.

In configurations where the sample probe 102 is used, the curtain port 108 can be used to push fluid flow over the tip of the sample probe 102 toward the pinhole 104, as well as to provide additional fluid flow, which can exit the inlet assembly 100 and prevent contaminants from entering the inlet assembly 100 (e.g., as illustrated in FIG. 1A). In this configuration, the fluid flow rate into the curtain port 108 is greater than the fluid flow rate out from the extraction port 106. For example, in one particular configuration, the flow rate through the extraction port 106 can be approximately two hundred milliliters per minute (200 ml/min), while the flow rate through the curtain port 108 can be approximately three hundred milliliters per minute (300 ml/min). In this configuration, the flow rate toward the pinhole 104 can be approximately twenty milliliters per minute (20 ml/min). In this configuration, an excess flow of eighty milliliters per minute (80 ml/min) exits the inlet assembly 100 (e.g., as illustrated in FIG. 1A), preventing contaminants from affecting the sample or minimizing contamination of the sample. However, these flow rates are provided by way of example only and are not meant to be restrictive of the present disclosure. Thus, other flow rates can be used with the inlet assembly 100.

In other instances, the curtain port 108 can be used when a sample detector is operated in a vapor sampling configuration. In this configuration, a sample probe 102 is not necessarily used to provide a sample of interest. Rather, air from outside the detector (e.g., ambient air) can be drawn in through the inlet assembly 100. This airflow can be generated and/or facilitated by fluid flow through the extraction port 106. For example, the rate of fluid flow through the extraction port 106 can be substantially greater than the rate of fluid flow through the curtain port 108 to draw air towards the inlet assembly 100. The fluid flow through the curtain port 108 can be used to guide fluid away from interior surfaces of the inlet assembly 100 and toward the pinhole 104, which can reduce contamination effects.

While the present disclosure and the accompanying figures describe an annular curtain port 108 configured to provide substantially uniform airflow around the periphery of the sample probe 102, it should be noted that this particular configuration is provided by way of example only and is not meant to be restrictive of the present disclosure. Thus, in other implementations, other variously-shaped curtain ports may be provided, including square-shaped apertures, rectangular-shaped apertures, elliptical-shaped apertures, diamond-shaped apertures, and so forth. Further, more than one aperture may be provided, including two apertures, three apertures, four apertures, and so forth. These additional apertures may be variously-shaped (e.g., as previously described). Further, it should be noted that the flow generated by these other aperture configurations may not be substantially uniform.

In implementations, fluid flow through the curtain port 108 can be cleaned and/or dried to remove potential contaminants. For example, ambient air pulled in from outside a housing of an IMS detector device using a fan, or the like, can be cleaned using a charcoal filter and supplied to the curtain port 108. In other implementations, airflow can be supplied using a pump and/or a source of compressed air, such as a compressed air canister. Further, in some instances, a trigger, such as a sensor, can be used to turn on a fan when, for example, a sample probe is inserted and/or removed from the inlet assembly 100. Sensors can include, but are not necessarily limited to: optical sensors, mechanical sensors, proximity sensors, and so forth. In other instances, clean and/or dry air can be supplied to the curtain port 108 substantially continuously.

FIG. 2 is an illustration of a spectrometer system, such as an ion mobility spectrometer (IMS) system 200. Although IMS detection techniques are described herein, it should be noted that a variety of different spectrometers can benefit from the structures, techniques, and approaches of the present disclosure. It is the intention of this disclosure to encompass and include such changes. IMS systems 200 can include spectrometry equipment that employs unheated (e.g., surrounding (ambient or room) temperature) detection techniques. For example, an IMS system 200 can be configured as a lightweight explosive detector. However, it should be noted that an explosive detector is provided by way of example only and is not meant to be restrictive of the present disclosure. Thus, techniques of the present disclosure may be used with other spectrometry configurations. For example, an IMS system 200 can be configured as a chemical detector. Further, in other implementations, IMS systems 200 can employ heated detection techniques. For example, an IMS system 200 can be configured as a gently heated detector, a fully heated detector, and so forth. An IMS system 200 can include a detector device, such as a sample detector 202 having a sample receiving port for introducing material from a sample of interest to an ionization region/chamber. For example, the sample detector 202 can have an inlet 204 where air to be sampled is admitted to the sample detector 202. In example implementations, the inlet 204 can be configured in the manner of the inlet assembly 100 previously described. In some implementations, the sample detector 202 can have another device such as a gas chromatograph (not shown) connected in line with the IMS inlet 204.

The inlet 204 can employ a variety of sample introduction approaches. In some instances, a flow of air can be used. In other instances, IMS systems 200 can use a variety of fluids and/or gases to draw material into the inlet 204. Approaches for drawing material through the inlet 204 include the use of fans, pressurized gases, a vacuum created by a drift gas flowing through a drift region/chamber, and so forth. For example, the sample detector 202 can be connected to a sampling line, where air from the surrounding environment (e.g., room air) is drawn into the sampling line using a fan. IMS systems 200 can operate at substantially ambient pressure, although a stream of air or other fluid can be used to introduce sample material into an ionization region. In other instances, IMS systems 200 can operate at lower pressures (i.e., pressures less than ambient pressure). Further, IMS systems 200 can include other components to furnish introduction of material from a sample source. For example, a desorber, such as a heater, can be included with an IMS system 200 to cause at least a portion of a sample to vaporize (e.g., enter its gas phase) so the sample portion can be drawn into the inlet 204. For instance, a sample probe, a swab, a wipe, or the like, can be used to obtain a sample of interest from a surface. The sample probe can then be used to deliver the sample to the inlet 204 of an IMS system 200. IMS systems 200 can also include a pre-concentrator to concentrate or cause a bolus of material to enter an ionization region.

A portion of a sample can be drawn through a small aperture inlet (e.g., a pinhole 104) into the sample detector 202 using, for example, a diaphragm in fluid communication with a volume of the sample detector 202. For instance, when the internal pressure in the volume is reduced by movement of the diaphragm, a portion of the sample is transferred from the inlet 204 into the sample detector 202 through the pinhole 104. After passing through the pinhole 104, the sample portion enters a detection module 206. The detection module 206 can include an ionization region where the sample is ionized using an ionization source, such as a corona discharge ionizer (e.g., having a corona discharge point). However, a corona discharge ionizer is provided by way of example only and is not meant to be restrictive of the present disclosure. Other example ionization sources include, but are not necessarily limited to: radioactive and electrical ionization sources, such as a photoionization source, an electrospray source, a matrix assisted laser desorption ionization (MALDI) source, a nickel 63 source ($Ni^{63}$), and so forth. In some instances, the ionization source can ionize material from a sample of interest in multiple steps. For example, the ionization source can generate a corona that ionizes gases in the ionization region that are subsequently used to ionize the material of interest. Example gases include, but are not necessarily limited to: nitrogen, water vapor, gases included in air, and so forth.

In implementations, the detection module 206 can operate in positive mode, negative mode, switch between positive and negative mode, and so forth. For example, in positive mode the ionization source can generate positive ions from a sample of interest, while in negative mode the ionization source can generate negative ions. Operation of the detection module 206 in positive mode, negative mode, or switching between positive and negative mode can depend on implementation preferences, a predicted sample type (e.g., explosive, narcotic, toxic industrial chemicals), and so forth.

Further, the ionization source can be pulsed periodically (e.g., based upon sample introduction, gate opening, the occurrence of an event, and so on).

The sample ions can then be directed toward a gating grid using an electric field. The gating grid can be opened momentarily to allow small clusters of sample ions to enter a drift region. For example, the detection module 206 can include an electronic shutter or gate at the inlet end of a drift region. In implementations, the gate controls entrance of ions to the drift region. For example, the gate can include a mesh of wires to which an electrical potential difference is applied or removed. The drift region has electrodes (e.g., focusing rings) spaced along its length for applying an electric field to draw ions along the drift region and/or to direct the ions toward a detector disposed generally opposite the gate in the drift region. For example, the drift region, including the electrodes, can apply a substantially uniform field in the drift region. The sample ions can be collected at a collector electrode, which can be connected to analysis instrumentation for analyzing the flight times of the various sample ions. For instance, a collector plate at the far end of the drift region can collect ions that pass along the drift region.

The drift region can be used to separate ions admitted to the drift region based on the individual ions' ion mobility. Ion mobility is determined by the charge on an ion, an ion's mass, geometry, and so forth. In this manner, IMS systems 200 can separate ions based on time of flight. The drift region can have a substantially uniform electrical field that extends from the gate to a collector. The collector can be a collector plate (e.g., a Faraday plate) that detects ions based on their charge as they contact the collector plate. In implementations, a drift gas can be supplied through the drift region in a direction generally opposite the ions' path of travel to the collector plate. For example, the drift gas can flow from adjacent to the collector plate toward the gate. Example drift gases include, but are not necessarily limited to: nitrogen, helium, air, air that is re-circulated (e.g., air that is cleaned and/or dried) and so forth. For example, a pump can be used to circulate air along the drift region against the direction of flow of ions. The air can be dried and cleaned using, for instance, a molecular sieve pack.

In implementations, the sample detector 202 can include a variety of components to promote identification of a material of interest. For example, the sample detector 202 can include one or more cells containing a calibrant and/or a dopant component. Calibrant can be used to calibrate the measurement of ion mobility. Dopant can be used to prohibit the ionization of interferant ions. Dopant can also be combined with a sample material and ionized to form an ion that can be more effectively detected than an ion that corresponds to the sample material alone. Dopant can be provided to one or more of the inlet 204, the ionization region and/or the drift region. The sample detector 202 can be configured to provide dopant to different locations, possibly at different times during operation of the sample detector 202. The sample detector 202 can be configured to coordinate dopant delivery with operation of other components of an IMS system 200.

A controller 250 can detect the change in charge on the collector plate as ions reach it. Thus, the controller 250 can identify materials from their corresponding ions. In implementations, the controller 250 can also be used to control opening of the gate to produce a spectrum of time of flight of the different ions along the drift region. For example, the controller 250 can be used to control voltages applied to the gate. Operation of the gate can be controlled to occur periodically, upon the occurrence of an event, and so forth. For example, the controller 250 can adjust how long the gate is open and/or closed based upon the occurrence of an event (e.g., corona discharge), periodically, and so forth. Further, the controller 250 can switch the electrical potential applied to the gate based upon the mode of the ionization source (e.g., whether the detection module 206 is in positive or negative mode). In some instances, the controller 250 can be configured to detect the presence of explosives and/or chemical agents and provide a warning or indication of such agents on an indicator 258.

In implementations, an IMS system 200, including some or all of its components, can operate under computer control. For example, a processor can be included with or in an IMS system 200 to control the components and functions of IMS systems 200 described herein using software, firmware, hardware (e.g., fixed logic circuitry), manual processing, or a combination thereof. The terms "controller" "functionality," "service," and "logic" as used herein generally represent software, firmware, hardware, or a combination of software, firmware, or hardware in conjunction with controlling the IMS systems 200. In the case of a software implementation, the module, functionality, or logic represents program code that performs specified tasks when executed on a processor (e.g., CPU or CPUs). The program code may be stored in one or more computer-readable memory devices (e.g., internal memory and/or one or more tangible media), and so on. The structures, functions, approaches, and techniques described herein can be implemented on a variety of commercial computing platforms having a variety of processors.

Figure 2B:
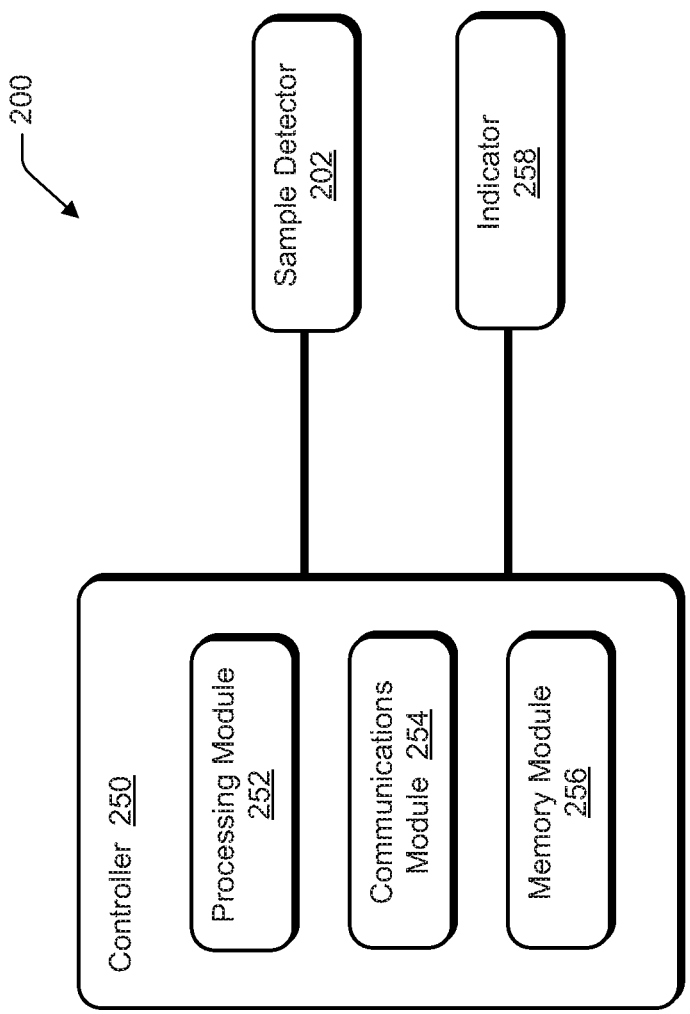
FIG. 2B is a diagrammatic illustration of a system including a controller operatively coupled with a sample detector, where the controller can be used to control the operation of an exhaust module to operate the sample detector in one or more of a sample probe configuration and a vapor sampling configuration in accordance with example implementations of the present disclosure.

For example, as illustrated in FIG. 2B, the sample detector 202 may be coupled with the controller 250 for controlling the extraction of fluids from the extraction port 106 and/or the curtain port 108. For instance, the controller 250 may be coupled with an exhaust module 208, which may include one or more fans (e.g., a battery powered fan), valves, louvers, vents, and so forth for controlling the extraction of fluids from the inlet 204 of the sample detector 202, e.g., by controlling the flow rate of fluid expelled from the extraction port 106 of the inlet 204 and/or by controlling the flow rate of fluid expelled from the curtain port 108 of the inlet 204. Thus, in configurations using both an extraction port 106 and a curtain port 108, fluid flow rates can be independently controllable for the extraction port 106 and the curtain port 108, such as to enable switching between configurations using a sample probe and configurations furnishing vapor sampling.

The controller 250 may include a processing module 252, a communications module 254, and a memory module 256. The processing module 252 provides processing functionality for the controller 250 and may include any number of processors, micro-controllers, or other processing systems, and resident or external memory for storing data and other information accessed or generated by the controller 250. The processing module 252 may execute one or more software programs, which implement techniques described herein. The processing module 252 is not limited by the materials from which it is formed or the processing mechanisms employed therein, and as such, may be implemented via semiconductor(s) and/or transistors (e.g., using electronic integrated circuit (IC) components), and so forth.

The communications module 254 is operatively configured to communicate with components of the sample detector 202. The communications module 254 is also communicatively coupled with the processing module 252 (e.g., for communicating inputs from the sample detector 202 to the processing module 252). The communications module 254 and/or the processing module 252 can also be configured to communicate with a variety of different networks, including, but not necessarily limited to: the Internet, a cellular telephone network, a local area network (LAN), a wide area network (WAN), a wireless network, a public telephone network, an intranet, and so on.

The memory module 256 is an example of tangible computer-readable media that provides storage functionality to store various data associated with operation of the controller 250, such as software programs and/or code segments, or other data to instruct the processing module 252 and possibly other components of the controller 250 to perform the steps described herein. Thus, the memory can store data, such as a program of instructions for operating the IMS system 200 (including its components), spectral data, and so on. Although a single memory module 256 is shown, a wide variety of types and combinations of memory (e.g., tangible memory, non-transitory) may be employed. The memory module 256 may be integral with the processing module 252, may comprise stand-alone memory, or may be a combination of both.

The memory module 256 may include, but is not necessarily limited to: removable and non-removable memory components, such as Random Access Memory (RAM), Read-Only Memory (ROM), Flash memory (e.g., a Secure Digital (SD) memory card, a mini-SD memory card, and/or a micro-SD memory card), magnetic memory, optical memory, Universal Serial Bus (USB) memory devices, hard disk memory, external memory, and other types of computer-readable storage media. In implementations, the sample detector 202 and/or memory module 256 may include removable Integrated Circuit Card (ICC) memory, such as memory provided by a Subscriber Identity Module (SIM) card, a Universal Subscriber Identity Module (USIM) card, a Universal Integrated Circuit Card (UICC), and so on.

In implementations, a variety of analytical devices can make use of the structures, techniques, approaches, and so on described herein. Thus, although IMS systems 200 are described herein, a variety of analytical instruments may make use of the described techniques, approaches, structures, and so on. These devices may be configured with limited functionality (e.g., thin devices) or with robust functionality (e.g., thick devices). Thus, a device's functionality may relate to the device's software or hardware resources, e.g., processing power, memory (e.g., data storage capability), analytical ability, and so on.

In an embodiment there is provided a system comprising: a sample detector comprising a sample receiving port; an inlet assembly configured to be positioned adjacent to the sample receiving port of the sample detector, the inlet assembly defining a volume for receiving a sample and comprising a gap defining an extraction port configured for extracting a first fluid flow to facilitate a the second fluid flow toward the sample receiving port; and an exhaust module for exhausting air from the extraction port. In this embodiment the system may comprise the features of the system defined in any of the appended claims.

An apparatus includes a sample receiving port and an inlet assembly configured to be positioned adjacent to the sample receiving port. The inlet assembly defines a volume for receiving a sample and includes a gap that defines an extraction port. The extraction port is configured to extract one fluid flow to facilitate another fluid flow toward the sample receiving port. The extraction port can be configured as an annular flow port around the sample receiving port. In some instances, the apparatus also includes a curtain port positioned apart from the sample receiving port and the extraction port. The curtain port can be used to guide fluid away from interior surfaces of the inlet assembly and toward the sample receiving port, and/or to provide an environment of controlled air, and/or to isolate the sample receiving port from external sources of contamination Although the subject matter has been described in language specific to structural features and/or methodological acts, it is to be understood that the subject matter defined in the appended claims is not necessarily limited to the specific features or acts described. Although various configurations are discussed the apparatus, systems, subsystems, components and so forth can be constructed in a variety of ways without departing from this disclosure. Rather, the specific features and acts are disclosed as example forms of implementing the claims.

What is claimed is:

1. A system comprising:
a sample detector comprising a sample receiving port configured to obtain a sample from a fluid flow to be analysed by the sample detector,
an extraction port arranged to draw the fluid flow toward the extraction port for sampling by the sample receiving port, wherein the extraction port is arranged relative to the sample receiving port so that the fluid flow towards the extraction port at least partially surrounds the sample receiving port,
an inlet assembly for receiving a sample probe arranged to enable a probe inserted to the inlet assembly to provide a sample into the fluid flow; and
a curtain port, spaced from the extraction port in the inlet assembly to provide a fluid to flow towards the extraction port around the probe.

2. The system as recited in claim 1, wherein the extraction port is separate from, and at least partially surrounds, the sample receiving port.

3. The system as recited in claim 1, wherein the extraction port is configured so that the fluid flow towards the sample receiving port is uniformly distributed about the sample receiving port.

4. The system as recited in claim 1, wherein the sample receiving port passes through a surface comprising the extraction port.

5. The system as recited in claim 4, wherein at least a part of the sample receiving port is coplanar with the extraction port.

6. The system as recited in claim 1, wherein the fluid flow comprises a first fluid flow portion, and a second fluid flow portion, the system comprising: an inlet assembly configured to be positioned adjacent to the sample receiving port of the sample detector, the inlet assembly defining a volume for receiving a sample and comprising a gap defining the extraction port configured for extracting the first fluid flow portion to facilitate the second fluid flow portion toward the sample receiving port; and an exhaust module for exhausting air from the extraction port.

7. The system as recited in claim 6, wherein the extraction port is at least partially circumferentially disposed around the sample receiving port.

8. The system as recited in claim 6, wherein the inlet assembly further defines the curtain port configured to be positioned apart from the sample receiving port and the extraction port for supplying a third fluid flow portion of the fluid flow to facilitate the second fluid flow toward the sample receiving port.

9. The system as recited in claim 8, wherein the inlet assembly is configured to receive a sample probe, the curtain port at least partially circumferentially disposed around a tip of a sample probe when the sample probe is inserted in the inlet assembly.

10. A system comprising:
    a sample detector comprising a sample receiving port configured to obtain a sample from a fluid flow to be analysed by the sample detector, and
    an extraction port arranged to draw the fluid flow toward the extraction port for sampling by the sample receiving port, wherein the extraction port is arranged relative to the sample receiving port so that the fluid flow towards the extraction port at least partially surrounds the sample receiving port, wherein the fluid flow comprises a first fluid flow portion, and a second fluid flow portion, the system further comprising:
    an inlet assembly configured to be positioned adjacent to the sample receiving port of the sample detector, the inlet assembly defining a volume for receiving a sample and comprising a gap defining the extraction port configured for extracting the first fluid flow portion to facilitate the second fluid flow portion toward the sample receiving port; and
    an exhaust module for exhausting air from the extraction port,
    wherein the inlet assembly further defines a curtain port configured to be positioned apart from the sample receiving port and the extraction port for supplying a third fluid flow portion of the fluid flow to facilitate the second fluid flow toward the sample receiving port, and
    wherein the inlet assembly is configured to receive a sample probe, the curtain port at least partially circumferentially disposed around a tip of a sample probe when the sample probe is inserted in the inlet assembly.

\* \* \* \* \*